United States Patent
Schauderna

(10) Patent No.: US 12,138,437 B2
(45) Date of Patent: Nov. 12, 2024

(54) PRESSURE SENSOR ASSEMBLY AND METHODS FOR INJECTION DEVICES

(71) Applicant: Sanofi, Paris (FR)

(72) Inventor: Florian Schauderna, Frankfurt am Main (DE)

(73) Assignee: Sanofi, Paris (FR)

( * ) Notice: Subject to any disclaimer, the term of this patent is extended or adjusted under 35 U.S.C. 154(b) by 996 days.

(21) Appl. No.: 16/965,662

(22) PCT Filed: Feb. 1, 2019

(86) PCT No.: PCT/EP2019/052463
§ 371 (c)(1),
(2) Date: Jul. 29, 2020

(87) PCT Pub. No.: WO2019/149868
PCT Pub. Date: Aug. 8, 2019

(65) Prior Publication Data
US 2021/0038833 A1   Feb. 11, 2021

(30) Foreign Application Priority Data

Feb. 5, 2018  (EP) .................................... 18305113
Feb. 7, 2018  (EP) .................................... 18305127

(51) Int. Cl.
*A61M 5/48* (2006.01)
*A61M 5/315* (2006.01)

(52) U.S. Cl.
CPC ........ *A61M 5/486* (2013.01); *A61M 5/31545* (2013.01); *A61M 5/3157* (2013.01);
(Continued)

(58) Field of Classification Search
CPC ................ A61M 5/3157; A61M 5/486; A61M 5/31545; A61M 2205/18;
(Continued)

(56) References Cited

U.S. PATENT DOCUMENTS

2011/0009821 A1* 1/2011 Jespersen ............ A61M 5/1452
                                                                    604/131
2011/0264033 A1 10/2011 Jensen et al.
(Continued)

FOREIGN PATENT DOCUMENTS

JP   2014-533539 A   12/2014
JP   2015-532862 A   11/2015
(Continued)

OTHER PUBLICATIONS

PCT International Preliminary Report on Patentability in International Appln. No. PCT/EP2019/052463, dated Aug. 11, 2020, 10 pages.
PCT International Search Report and Written Opinion in International Appln. No. PCT/EP2019/052463, dated Mar. 15, 2019, 15 pages.

*Primary Examiner* — Phillip A Gray
*Assistant Examiner* — Rachel T. Smith
(74) *Attorney, Agent, or Firm* — Fish & Richardson P.C.

(57) ABSTRACT

Described is an electronics assembly with pressure or force sensing capabilities for use in a drug delivery device. The electronics assembly includes a processor, a sensor arranged to measure the force applied by a drive mechanism to drive a medicament from a cartridge, a wireless module to which an external device can be paired, a power module arranged to supply power to the assembly, and memory storing instructions for the processor to perform. The instructions include receiving a measurement signal during the drug delivery operation, and determining if the dose of the medicament was expelled from the drug delivery device based on the received measurement signal.

9 Claims, 11 Drawing Sheets

(52) U.S. Cl.
CPC . *A61M 2205/18* (2013.01); *A61M 2205/3306* (2013.01); *A61M 2205/332* (2013.01); *A61M 2205/3331* (2013.01); *A61M 2205/3368* (2013.01); *A61M 2205/3375* (2013.01); *A61M 2205/3584* (2013.01); *A61M 2205/52* (2013.01); *A61M 2205/581* (2013.01); *A61M 2205/582* (2013.01); *A61M 2205/583* (2013.01); *A61M 2205/8206* (2013.01)

(58) Field of Classification Search
CPC .... A61M 2205/3306; A61M 2205/332; A61M 2205/3331; A61M 2205/3368; A61M 2205/3375; A61M 2205/3584; A61M 2205/52; A61M 2205/581; A61M 2205/582; A61M 2205/583; A61M 2205/8206; A61M 2005/2474; A61M 2205/33; A61M 2205/3569; A61M 2205/8212; A61M 5/31568

See application file for complete search history.

(56) References Cited

U.S. PATENT DOCUMENTS

| | | | |
|---|---|---|---|
| 2015/0289896 A1 | 10/2015 | Gomi et al. | |
| 2016/0259913 A1 | 9/2016 | Yu et al. | |
| 2017/0312455 A1* | 11/2017 | Mirov | A61M 5/31511 |
| 2018/0043105 A1* | 2/2018 | Nazzaro | A61M 5/1452 |
| 2018/0353682 A1* | 12/2018 | Laurence | G16H 20/17 |

FOREIGN PATENT DOCUMENTS

| | | |
|---|---|---|
| WO | WO 2013/054165 | 4/2013 |
| WO | WO 2013/076026 A1 | 5/2013 |
| WO | WO 2014/067879 A1 | 5/2014 |
| WO | WO 2014/145906 | 9/2014 |
| WO | WO 2017/165207 | 9/2017 |
| WO | WO 2017/189153 | 11/2017 |

* cited by examiner

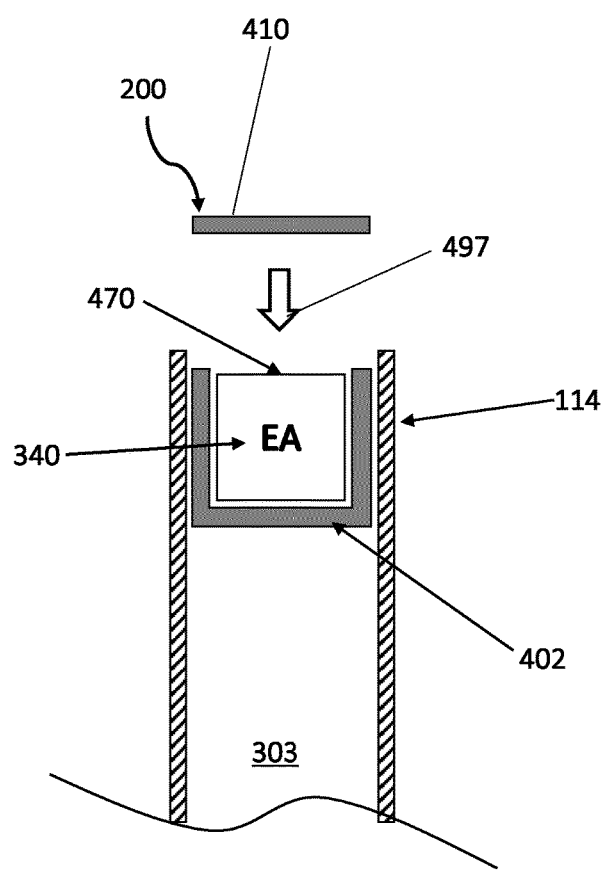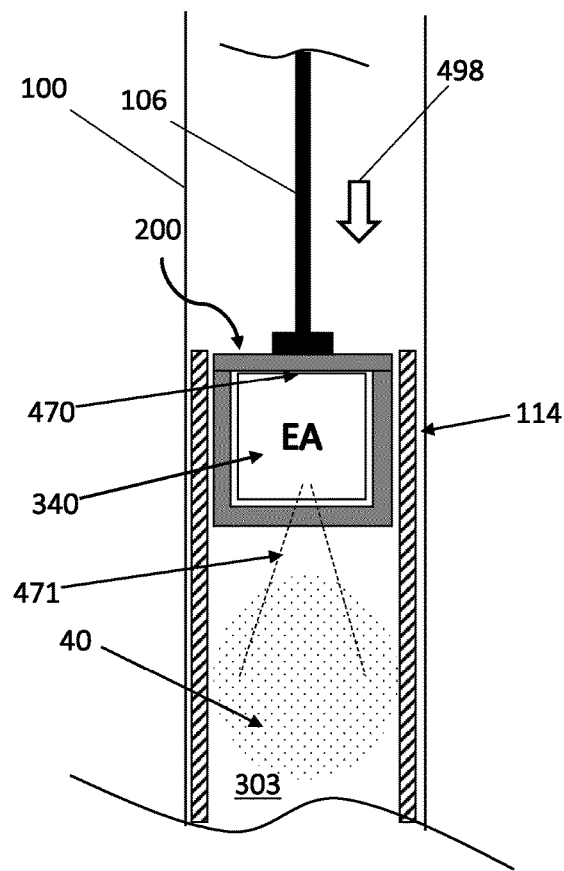
FIG. 4A
FIG. 4B

PRESSURE SENSOR ASSEMBLY AND METHODS FOR INJECTION DEVICES

CROSS REFERENCE TO RELATED APPLICATIONS

The present application is the national stage entry of International Patent Application No. PCT/EP2019/052463, filed on Feb. 1, 2019, and claims priority to Application No. EP 18305127.5, filed on Feb. 7, 2018, and Application No. EP 18305113.5, filed Feb. 5, 2018, the entire disclosures of which are incorporated herein by reference.

TECHNICAL FIELD

This description relates to an electronics assembly with pressure or force sensing capabilities for use in a drug delivery device.

BACKGROUND

A variety of diseases exist that require treatment by injection of a medicament. Such injections can be performed using drug delivery devices, which can be applied either by medical personnel or by patients themselves. As an example, type-1 and type-2 diabetes can be treated by patients themselves by injection of drug doses, for example once or several times per day. For instance, a pre-filled disposable drug pen or autoinjector can be used as a drug delivery device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use.

SUMMARY

This disclosure relates to drug delivery devices having electronics capable of sensing pressure or force in the drug delivery device, specifically, in some instances, during a drug delivery operation in order to determine a quality of the drug delivery operation. In some instances, a force sensor is disposed in or around a cartridge being acting upon by a plunger rod of the drug delivery device, or in the plunger rod itself, in order to sense the force applied to a medicament in the cartridge. In other, the electronics and/or pressure sensor are housed directly within the bung or stopper of the cartridge.

In a representative overview, an electronics assembly is inserted into the stopper of the cartridge. A pressure sensor in the electronics assembly detects pressure or force put on the stopper of the cartridge by the plunger rod as a head of the plunger rod contacted the stopper and drives the stopper into the cartridge to force a medicament from the cartridge. In some instances, the position of the plunger rod or stopper is also detected. The shape of the pressure curve (e.g., pressure vs. time) in the cartridge or plunger rod varies as the drug delivery operation occurs and the pressure sensor of the electronics assembly senses this change and can, in some instances, use the sensed to calculate an indication of the quality of the drug delivery operation. The indication may represent a successful completion of the drug delivery operation, or indicate a calculated amount of medicament that was delivered, which may be less than the expected amount due to one or more possible failure modes, which can also be indicated.

For example, a drug delivery pathway (e.g., a needle) may be blocked or constricted, which raises the pressure in the cartridge during delivery. In another example, the initial construction or priming of the drug delivery device may leave a head of the plunger rod spaced a small distance away from the stopper of the cartridge, which, during a subsequent drug delivery operation, will result in an initial period of movement of the plunger rod without an increase in pressure on the stopper (i.e., less medicament than expected is expelled from the cartridge). In some instances, this electronics assembly includes a Bluetooth or other wireless module configured to send the sensed pressure signal and/or the calculated indication of the quality of the drug delivery operation to an external device in order to present the information to a user. In other instances, or in addition, the drug delivery device may include an alert mechanism (e.g., an audible or visible feedback mechanism), which is connected to the electronics assembly and is configured to alert the user of a successful drug delivery operation or of any issues detected during the drug delivery operation based on the sensed pressure.

In some instances, the pressure sensor detecting a drug delivery operation activates a wireless module in the electronics assembly, such that the patient is able to pair or link an external device with the electronics assembly to receive a transmission containing the sensed pressure data or other calculated information (e.g., the delivered dose and/or the quality indication) after the drug delivery operation. After each detected injection, a new transfer of the sensed data to the external device is possible. As an additional feature, the electronics assembly can transmit additional data, besides the sensed pressure or calculated indication of quality described above. For example, the electronics assembly can store and transmit batch or expiration information related to the drug delivery device and/or the medicament contained in the cartridge. This additional information enables a user to ensure that their external device is paired to the correct drug delivery device, and that the medicament contained therein is not expired. While some examples herein disclose a pressure sensor, one skilled in the art will appreciate that force sensors are also able to provide the sensing capabilities and that the term force sensor and pressure sensor are used depending on the location of the sensing (e.g., a force sensor to sense a force of the drive mechanism, and a pressure sensor to measure a pressure applied to a medicament in a cartridge by a stopper).

In a representative example, an electronics assembly is arranged in a cartridge or otherwise positioned in a drug delivery device to enable a pressure sensor of the electronics assembly to detect changes in pressure applied to a stopper of a cartridge by a drive mechanism of the drug delivery device that is used for changing the fill level of the cartridge (e.g., a filling operation or a drug delivery operation). The electronics assembly includes a processor configured to calculate an indication of the quality of the drug delivery operation, and enables a data exchange via Bluetooth wireless module, or similar wireless protocol, upon determining that a drug delivery operation has taken place. A benefit of this arrangement is that, in some instances, no external activation of the electronics assembly is required, which enables the electronics assembly to be a self-contained (e.g., sealed) assembly after production and before introduction to the cartridge or drug delivery device. In some instances, the drug delivery device include a sensor configured to detect the activation of the drive mechanism and provide this information to the electronics assembly with the pressure sensor, in order for the electronics assembly to detect a priming gap that exists when the initiation of a drug delivery operation does not result an immediate increase in the pressure in the cartridge as a result of a gap between the plunger rod and the stopper. In operation, a priming gap must be taken up by the movement of the plunger rod during the first moments of the drug delivery operation, and this can results in less medicament being expelled than expected based on the change in the position of the plunger rod alone.

Examples of the electronics assembly can be used in both single-use (e.g., disposable) drug delivery devices, and multi-use (e.g., reusable) drug delivery devices. In a reusable drug delivery device example, an electronics assembly is constructed and assembled with a pre-filled cartridge.

Certain aspects of the present disclosure result in several advantages beyond the addition of pressure sensing and wireless connectivity to the drug delivery device. For example, a drug delivery device has many possible failure modes, some of which may be difficult to detect by a user of the drug delivery device. By sensing pressure applied by a drive mechanism, an electronics assembly in the drug delivery device is able to determine if a pressure profile during a drug delivery operation corresponds to an expected dose to be delivered during the drug delivery operation. In some instances, the sensed pressure alert the user to a problem with the drug delivery device, or just alert then when the drug delivery operation is completed and pressure inside the drug delivery device has normalized, which indicates that no further medicament is to be expelled from the device. In some instances, the sensed pressure can be used to alert a user that the drug delivery operation failed, or that less than the expected dose of medicament was delivered. In some instances, the sensed pressure is used to tag a delivered dose, e.g., when a user prime the pen as advised in the instructions (e.g., remove priming gap), the dose can be tagged as "safety shot" and will not be counted as "injected." This is relevant for using data for treatment algorithms. In some instances, the sensed pressure can be used to trigger an alert to the user, or to track the performance of a reusable drug delivery device.

In some instances, the pressure sensor is used to detect a property of the medicament, for example viscosity, during the drug delivery operation, and, in some instances, determine the temperature of the medicament or generate an alert to the user that the medicament was not being stored or delivered at a proper temperature. In other instances, the pressure sensor is configured to activate the internal electronics of an electronics assembly to extend the shelf life of a manufactured electronics assembly prior to introduction to a drug delivery device or cartridge. Similarly, in some instances, the pressure sensor is used to limit the activation of a wireless module activation until after a drug delivery operation, thereby further extending the shelf life of the electronics assembly after final manufacturing of the drug delivery device (i.e., in a ready to use state) by limiting operation of the wireless module. With an extended shelf life, electronics assemblies can be manufactured separately and independently from the manufacturing of the cartridge or drug delivery device, which also reduces or eliminates impact on existing production lines.

Another advantage is the ability for the electronics assembly to provide extra information to a user via the wireless transmission to the external device. For example, the drug delivery device or cartridge may be provided with an expiration date that can be transmitted to and stored in the external device to help the user confirm the printed information and better manage the drug delivery. Additional information, such as a batch number or unique serial number of the drug delivery device or cartridge can be transmitted to the external device to aid the user. This data can also be centrally tracked by the manufacturer to assist in recalls, track and analyze patient behavior, and monitor product usage. Additionally, in some embodiments, the electronics assembly includes a temperature sensor and the electronics assembly can provide temperature data to the external device to, for example, warn a user when a temperature limit has been reached. The temperature sensor also allows a manufacturer to track patient and transporter compliance with medicament temperature handling policies.

An example embodiment of the present disclosure is a drug delivery device including a housing, a drug container configured to be contained in the housing of the drug delivery device, the drug container includes a stopper configured to contain a medicament in the drug container, a drive mechanism configured to exert a force onto the stopper of the drug container to drive the stopper into the drug container and expel a dose of the medicament from the drug delivery device during a drug delivery operation, a processor, a pressure or force sensor arranged to measure the pressure or force applied by the drive mechanism and output a measurement signal to the processor, and at least one non-transitory computer readable medium storing instructions operable to cause the processor to perform operation. The operation include activating the pressure or force sensor during the drug delivery operation, receiving a measurement signal during the drug delivery operation, and determining if the dose of the medicament was expelled from the drug delivery device based on the received measurement signal.

In some examples, the non-transitory computer readable medium stores a reference measurement signal for the dose, and determining if the dose of the medicament was expelled includes comparing the received measurement signal to the reference measurement signal.

In some examples, the drug delivery device includes a dose selection mechanism configured to set the dose and output a dose signal to the processor corresponding to the set dose, the operations include receiving the dose signal and calculating a reference measuring signal for the dose, and determining if the dose of the medicament was expelled includes comparing the received measurement signal to the reference measurement signal.

In some examples, the instructions include comparing the pressure represented by the measurement signal to an expected maximum or minimum pressure, and determining if the dose of the medicament was expelled from the drug delivery device includes detecting a blocked fluid path condition based on the comparing.

In some examples, the operations calculating a time delay between an initiation of the drug delivery operation and an increase in the pressure represented by the measurement signal, and determining if the dose of the medicament was expelled from the drug delivery device includes detecting a priming gap between the drug container and the drive mechanism based on the time delay.

In some examples, wherein the operations include comparing the pressure represented by the measurement signal to an expected minimum pressure at the end of the drug delivery operation, and determining if the dose of the medicament was expelled from the drug delivery device includes determining when an internal pressure in the drive mechanism has normalized based on the comparing.

In some examples, the drug delivery device includes a wireless module configured to transmit a wireless signal to an external device, and the instructions include generating a drug delivery indication based on the determining if the dose of the medicament was expelled from the drug delivery device, and transmitting the drug delivery indication to the external device.

In some examples, the drug delivery device includes an alert mechanism configured to provide an audible, tactile, or visible alert to a user of the drug delivery device, and the operations include generating a drug delivery indication based on the determining if the dose of the medicament was expelled from the drug delivery device, and activating the alert mechanism based on the drug delivery indication.

In some examples, the drug delivery device includes a position sensor configured to detect the position of one or more of the stopper and the drive mechanism and output a position signal to the processor, and the instructions include receiving the position signal at least one of: before, during, and after the drug delivery operation. In addition, in some examples determining if the dose of the medicament was expelled from the drug delivery device is based on the received measurement signal and the received position signal.

In some examples, the pressure sensor is arranged in the stopper and configured measure the pressure in the medicament due to the force applied by the drive mechanism to the stopper. In some examples, the pressure or force sensor is disposed in a stopper or plunger of the drive mechanism.

Yet another example is an electronics assembly for use in a drug delivery device. The electronics assembly includes a processor, a pressure or force sensor arranged to measure the force applied by a drive mechanism of the drug delivery device and output a measurement signal to the processor, and at least one non-transitory computer readable medium storing instructions operable to cause the processor to perform operations. The operations include activating the pressure or force sensor during the drug delivery operation and receiving a measurement signal during the drug delivery operation, and determining if the dose of the medicament was expelled from the drug delivery device based on the received measurement signal.

In some examples, the pressure or force sensor is arranged to be disposed inside of a stopper, and wherein the stopper is configured to be inserted into a drug container for use with the drug delivery device. In some examples, the electronics assembly is configured to be inserted into the stopper. In some examples, the electronics assembly and/or the sensor is integrally formed with the stopper.

Still yet another example is a method of analyzing a drug delivery operation of a dose of medicament from of a drug delivery device using a pressure or force sensor. The method includes activating the sensor during the drug delivery operation and receiving a measurement signal during the drug delivery operation, and determining if the dose of the medicament was expelled from the drug delivery device based on the received measurement signal.

In some examples, the determining if the dose of the medicament was expelled includes comparing the received measurement signal to a reference measurement signal. In some examples, the method includes receiving a dose signal from a dose selection mechanism of the drug delivery device and calculating a reference measuring signal for the dose, and determining if the dose of the medicament was expelled includes comparing the received measurement signal to the reference measurement signal.

In some examples, the method includes comparing the pressure represented by the measurement signal time to an expected maximum pressure or force, and determining if the dose of the medicament was expelled from the drug delivery device includes detecting a blocked fluid path condition based on the comparing.

In some examples, the method includes calculating a time delay between of an initiation of the drug delivery operation and an increase in the pressure or force represented by the measurement signal, and determining if the dose of the medicament was expelled from the drug delivery device includes detecting a priming gap between the drug container and the drive mechanism based on the time delay.

In some examples, the method includes comparing the pressure or force represented by the measurement signal to an expected minimum pressure or force at the end of the drug delivery operation, and determining if the dose of the medicament was expelled from the drug delivery device includes determining when the drive mechanism has normalized based on the comparing.

In some examples, the method includes generating a drug delivery indication based on the determining, and activating an alert mechanism of the drug delivery device based on the drug delivery indication.

In some examples, the method includes generating a drug delivery indication based on the determining, and wirelessly transmitting the drug delivery indication to an external device.

BRIEF DESCRIPTION OF THE FIGURES

FIG. 4A is a cross-sectional view of the electronics assembly and stopper of FIGS. 2A-2C being disposed in the drug delivery device of FIG. 1.

FIG. 4B is a cross-sectional view of the electronics assembly and stopper of FIG. 4A disposed in the drug delivery device of FIG. 1 in a ready-to-use configuration.

DETAILED DESCRIPTION

Figure 1:
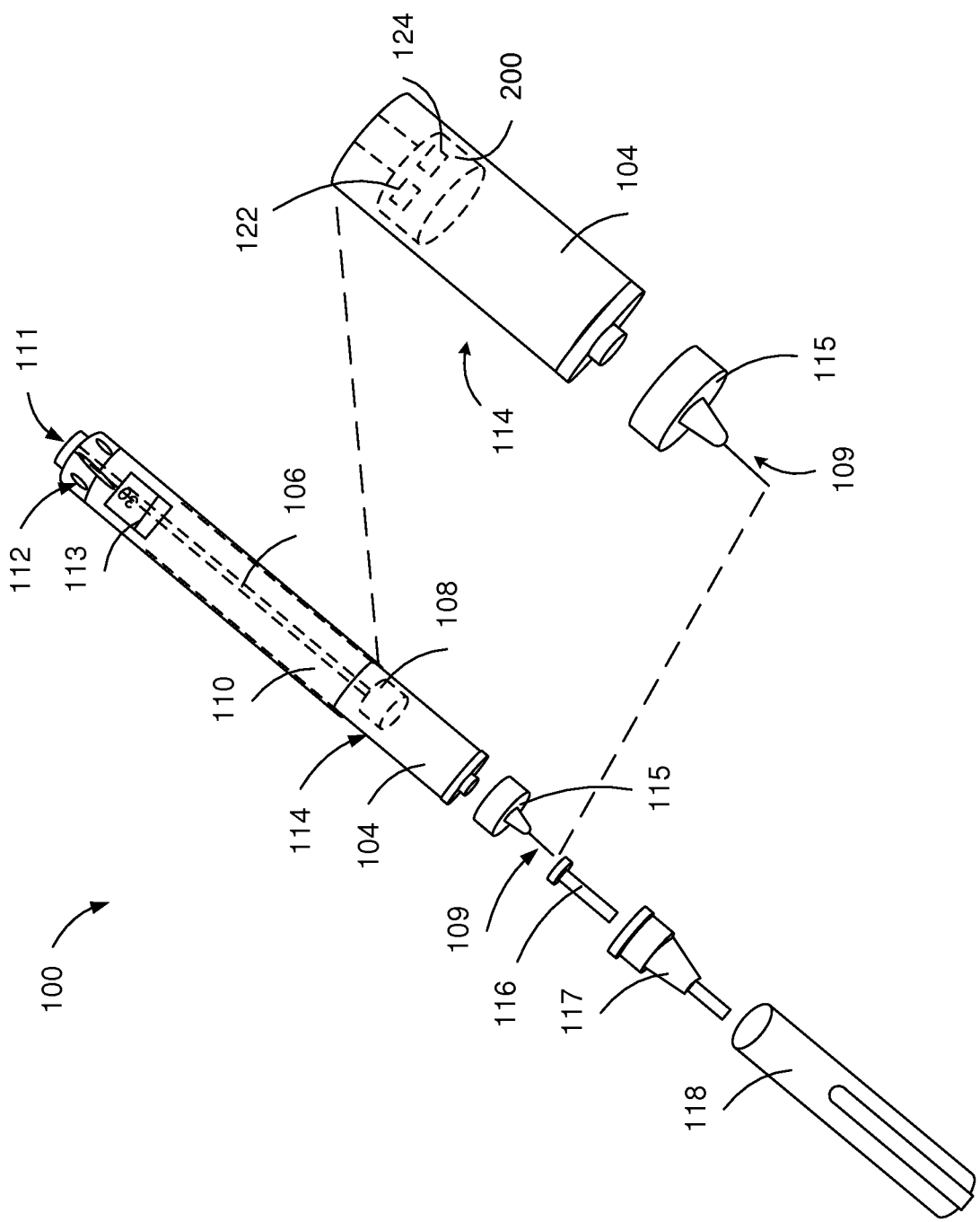
FIG. 1 is an exploded view of a drug delivery device that includes a stopper.

Cartridge-based injection and medical syringe systems often include integrated electronics that support the incorporation of an internal pressure sensor along with, in some instances, wireless connectivity. In some examples, a cartridge stopper (sometimes referred to as a bung) can include a self-contained electronics assembly, including a pressure or force sensor, a wireless module, a power module, and a processor with memory. For example, a stopper may accept an insertable electronic assembly that is separated from the stopper. The stopper, for example, can be assembled into the stopper or cartridge after sterilization. The electronics assembly can be a self-contained unit that is constructed prior to assembly of the drug delivery device and embedded in the stopper during a final assembly of the drug delivery device. In some examples, the self-contained electronics assembly enables detection of the pressure in the cartridge or the force applied to the stopper and enables pairing (e.g., via Bluetooth or similar wireless protocols) with an external device to report the measured pressure or force during a drug delivery operation in order to determine whether or not the drug delivery operation was completed and if it was successful in delivering the intended dose. For example, a drug delivery device with a wireless module may enable a smartphone or tablet to pair with the drug delivery device to confirm that an injection has taken place or to receive a measurement from an internal pressure sensor providing a confirmation of an expelled dose. In other examples, the electronics assembly is integrated into the plunger rod or drive mechanism of the drug delivery device and arranged to measure the force applied to the stopper of the cartridge by the plunger rod.

A challenge exists in in detecting failed or incomplete drug delivery operations. Additionally, it can be important to detect when a drug delivery operation has completed, as a selected dose may only be completed delivered to a patient after the pressure or force in the drug delivery device has normalized (i.e., the internal components have relaxed). Examples of the present disclosure include using a pressure or force sensor to analyze the quality of a drug delivery operation and enable an indication of that quality to be generated. In some instances, this indication represents a confirmation that, according to the sensed pressure or force during the drug delivery operation, the drug delivery operation is completed and that the drug delivery operation delivered the expected dose of a medicament. While the completion of the drug delivery operation may be detectable based on the normalization of internal pressure or force, the indication that the expected dose of medicament was delivered is more complicated and depends on the shape of the detected force curve. For example, certain common failure modes of drug delivery devices can result in less than or no medicament being delivered during a drug delivery operation. In one example, the needle or medicament fluid pathway can become blocked, such that a subsequent drug delivery operation (e.g., force applied to a stopper in a cartridge), might not overcome the blockage and less than (or none) of the expected dose will be delivered (which, in some cases (e.g. small to medium doses, automated systems), may be unnoticed by the user/patient and is a typical hazard of undetected under-dosing).

A pressure or force sensor positioned to measure the force applied by to the cartridge will observe a higher than expected pressure reading as a result of the resistance of the blockage.

In another example, the plunger rod of a drug delivery device may not be positioned directly against a stopper of a cartridge prior to use. In this case, where a drug delivery operation involves a preset movement of the plunger rod, the initial movement of the plunger rod prior to contact with the stopper equates to a reduction in the delivered dose, as compared to the value expected based purely on the total displacement of the plunger rod. In this instance, a pressure or force sensor can measure the pressure or force and time the pressure or force was applied to the stopper and determine that the time was less than expected, or that the integral over time of the force applied to the stopper was less than expected. All three of these detection schemes (completion, blockage, and priming) are discussed in more detail below, and other detection are possible. For example, the sensor could also detect disassembly of the pen (drop force level), e.g., in reusable devices to detect and record a cartridge change event, t notify users for specific actions to be taken after disassembly (e.g., resetting the plunger), or to warn users about intended disassembly o insufficient assembly. For disposable devices, the sensor can be configured to provide counterfeit detection and warning (e.g., to detect if the device has been illegally disassembled and refilled).

In some examples of the present disclosure, a solution to these challenges involves a pressure sensor arranged in the stopper or the plunger rod to detect the pressure applied to the medicament during a drug delivery operation and subsequently determining, based on the detected pressure, an indication of the quality of the drug delivery operation. In addition, in some examples, a solution to second challenges involves using a position sensor to detect the position of the stopper or the plunger rod and compare it to the detected pressure in order to determine the indication of the quality of a drug delivery operation, as described in more detail below.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc.

Such variations can arise due to various factors, such as, for example, a drug ranging in viscosity from about 3 cP to about 50 cP.

The drug or medicament may be contained in a primary package, cartridge, or "drug container" adapted for use with a drug delivery device. The drug container may be, for example, a cartridge, syringe, reservoir, or other vessel configured to provide a suitable chamber for storage (e.g., short- or long-term storage) of one or more pharmaceutically active compounds. For example, in some embodiments, the chamber may be designed to store a drug for at least one day (e.g., 1 to at least 30 days). In some embodiments, the chamber may be designed to store a drug for about 1 month to about 2 years. Storage may occur at room temperature (e.g., about 20° C.), or refrigerated temperatures (e.g., from about −4° C. to about 4° C.). In some embodiments, the drug container may be or may include a dual-chamber cartridge configured to store two or more components of a drug formulation (e.g., a drug and a diluent, or two different types of drugs) separately, one in each chamber. In such embodiments, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance that is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-114, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or H Br salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

FIG. 1 is an exploded view of a drug delivery device 100, which may be a disposable or reusable drug delivery device. The drug delivery device 100 includes a housing 110 that contains a cartridge 114 and a cartridge housing 104 in which the cartridge 114 is disposed. A bung or stopper 200 is disposed in the body 104 of the cartridge 114 and can be advanced within the body 104 during use to expel medicament from the cartridge 114. A needle assembly 115 can be affixed to the cartridge housing 104. A needle 109 of the needle assembly 115, prior to use, is protected by an inner needle cap 116 and an outer needle cap 117, which in turn can be covered by a cap 118. A medicament or drug dose to be ejected from the drug delivery device 100 is selected by turning a dosage knob 112, and the selected dose is displayed via a dosage window or display 113.

As described further below, the drug delivery device 100 may include one or more electronic components 122, 124, some of which may be included in the stopper 200 of the cartridge 114, for example, as a self-contained electronics assembly. In some examples, the electronic components 122, 124 are located in other parts of the drug delivery device, while enabling a sensor of the electronic components 122, 124 to determine or measure a force applied to the stopper 200 the cartridge 114 by the plunger rod 106 or the force in the plunger rod 106 as applied by a drive mechanism of the drug delivery device. In some instances, the electronic components 122, 124 are located outside of the stopper 200, for example, where a force sensor is arranged on the plunger rod 106 to measure the applied force. In other instances, the electronic components 122, 124 are separated. For example, a force or pressure sensor may be arranged between the head of the plunger rod 106 and the stopper 200, and in electronic communication with electronic components located in the housing 110.

Continuing with the operation of the drug delivery device 100, turning the dosage knob 112 causes a mechanical click sound to provide acoustical feedback to a user. The numbers displayed in the dosage display 113 are printed on a sleeve that is contained in the housing 110 and mechanically interacts with a plunger configured to interact with the cartridge 114. When the needle 109 is stuck into a patient and then an injection button 111 is pushed, the drug dose displayed in the display 113 will be ejected from the drug delivery device 100. During an injection, a drive mechanism 106, which is shown as an outline of a plunger arm, drives the stopper 200 into the cartridge 114 to expel the drug. The stopper 200 acts as a barrier to prevent fluids and gases from leaking in and out of the cartridge 114, and can prevent evaporation of H2O and other fluids. In some embodiments, the seal function is provided by elastic sealing elements in contact with the container walls, but still allows the stopper 200 to glide. When the needle 109 of the drug delivery device 100 remains for a certain time in the skin of the patient after the injection button 111 is pushed, a high percentage of the dose is actually injected into the patient's body. In some examples, the drug delivery device 100 is a single use or disposable device, and one skilled in the art will appreciate that the electronic components 122, 124 used in the drug delivery device 100 can be similarly present with similar functions in a single use or disposable drug delivery device.

Figure 2B:
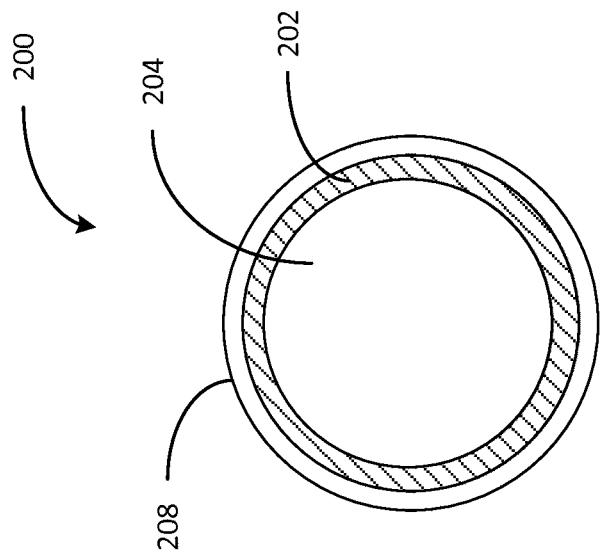
FIG. 2B is a top view of the stopper of FIG. 2A.
Figure 2A:
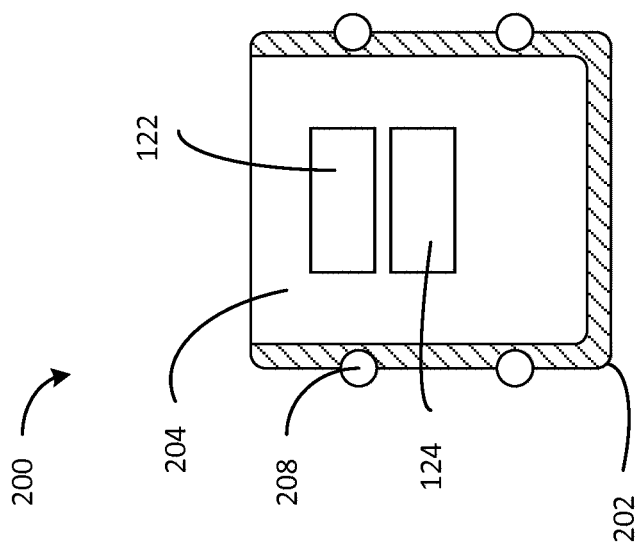
FIG. 2A is a cross sectional view of the stopper of FIG. 1 containing an electronics assembly.

FIG. 2A is a cross sectional view of an embodiment of the stopper 200 of the drug delivery device 100. The stopper 200 includes a shell 202 and a core 204 containing the electronic devices 122, 124, which, in some embodiments, are embedded into the material of the core 204. In some instances, the core 204 is configured to be inserted into the shell 202 of the stopper 200 after manufacturing. For example, the core 204 may be inserted into the shell 202 after the shell is disposed in the cartridge 114 of the drug delivery device 100. In other instances, the shell 202 is assembled with the core 204 having the electronic devices 122, 124 to be later inserted into the cartridge 114. In some instances, the shell 202 includes sealing elements 208 (e.g. o-rings) that are arranged to provide a sealing interface with an inner surface of the cartridge 114 when the shell 202 is inserted into the cartridge 114. In some instances, the shell 202 and core 204 are manufactured as a single component with or without the electronic devices 122, 124.

In some instances, the materials of the shell 202 and the core 204 are selected for their ability to allow a sensor signal to pass therethrough. For example, nonmetal materials like polymers or ceramics or very thin metal (e.g., <0.1 mm in thickness) may be used. The electronic devices 122, 124 may include, for example, a sensor, an energy source, a microcontroller, and/or a wireless transceiver. The electronic devices 122, 124 are representative only. There can be any number of electronic devices. The sensor may be a pressure-sensing or force-sensing device such as, for example, a piezoresistive strain gauge, a capacitive diaphragm and pressure cavity, an electromagnetic device, or a piezoelectric device. The pressure or force sensor may generate a signal responsive to the force applied by the plunger rod 106 to the stopper 200, or by the stopper 200 to a medicament in the cartridge 114, which, in some embodiments, is used to determine an amount of medicament driven from the cartridge 114 by the stopper 200 during a drug delivery operation, or to determine if an injection has occurred, been completed, or if a number of different possible failures occurred during the drug delivery operation. In some embodiments, a position sensor is also included to sense the position of the stopper 200 in the cartridge 114 or the position of the plunger rod 106 with respect to the cartridge 114 or stopper 200. The position of the stopper 200 before and after an injection corresponds to a change in volume of medicament remaining in the cartridge 114, which can indicate the volume or dose of the medicament expelled from the cartridge 114. The force applied to the stopper 200 by the plunger 106 also corresponds to a change in volume of medicament remaining in the cartridge 114, which can indicate the volume or dose of the medicament expelled from the cartridge 114 provided that the shape of the force applied to the stopper during the course of a drug delivery operation closely matches an expected value.

In some embodiments, the response received by the pressure or force and/or position sensor is provided to a controller (e.g. a processor located in the stopper 200 or elsewhere in the drug delivery device 100) which may receive the response and calculate a state of the cartridge 114. The state of the cartridge 114 may correspond to a position of the stopper 200, or an indication of the quality of a drug delivery operation.

In some embodiments, the energy source is a battery or other energy storing device. The wireless module may communicate with an external electronic device as well as with the sensor.

The external electronic device, which may be a controller, smart phone, tablet, or computer, may communicate data received from the sensor to an external database. The communication with the external device can be one way or bidirectional. Data transferred from the sensor device to an external database can contain information which is related to the identity of the device (e.g. a unique number), calibration data, production lot information, device material information, data related to storage time and production time, and information related to the sensor measurement (e.g., time of measurement, sensor measurement results like temperature, distances, light signals, and acoustic signals, etc.). The wireless module may communicate using any known wireless communication technique including, for example Bluetooth, NFC, or radio frequencies.

The shell 202 of the stopper 200, in some embodiments, is constructed from materials such as metals, polymers (e.g., COC, PA, PP, PE, POM, PS, ABS, COP, etc.), glass or ceramics. In some embodiments, the electronic devices (or electronic assembly) 122, 124 includes one or more of the following: a sensor, a power source (e.g. battery), a controller or processor, a wireless communication module (e.g. Bluetooth, NFC, Bluetooth LE, any RF, IrDA), memory, an on-off switch, a thermos-sensing element, a pressure or force sensor etc. In some embodiments, the electronics devices 122, 124 include an on-off mechanism configured to trigger the electronics devices 122, 124 by, for example, contact on the stopper 200 by a component of the drug delivery device 100 (e.g., force from a drive mechanism 106) during assembly of the drug delivery device 100. In some instances, the on-off mechanism is a pressure or force sensor.

FIG. 2B is a top view of the stopper 200. The shell 202 surrounds the core 204 and interfaces with the sealing element 208, which forms a sealing interface with the cartridge 114 upon the stopper's 200 introduction into the cartridge 114. The sealing interface may form at least part of a sterile barrier within the cartridge 114 to preserve the sterility of the medicament to be delivered by the drug delivery device 100.

Figure 2C:
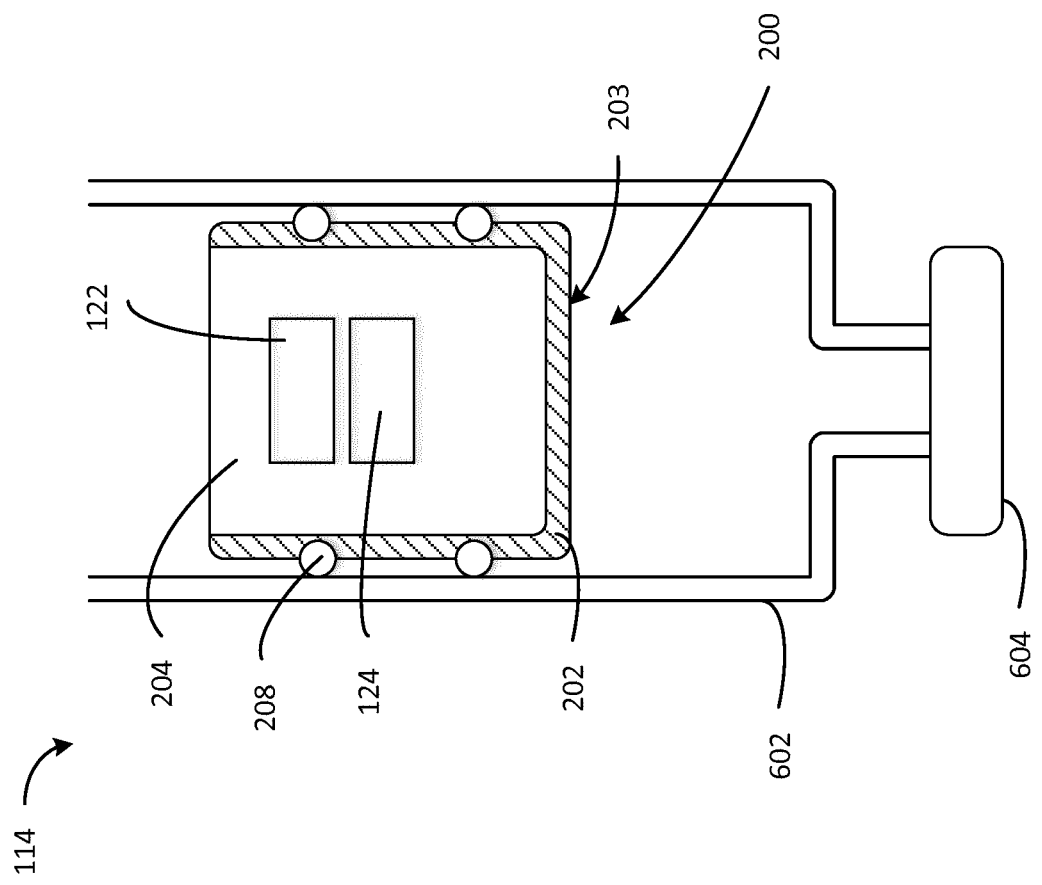
FIG. 2C is a cross sectional view of the stopper of FIG. 2A disposed in the cartridge of the drug delivery device of FIG. 1.

FIG. 2C is a cross-sectional view of the stopper 200 disposed in the cartridge 114. The various features of the stopper 200 shown are described above with respect to FIGS. 2A and 2B. The cartridge 114 includes a housing 602 that interfaces with the sealing element 208 of the stopper 200 to seal an open end of the cartridge 114. In some embodiments, a medicament is disposed in the space between the cap 604 of the cartridge 114 and the shell 202 of the stopper 200.

In some embodiments, different measuring methodologies are used to measure the pressure applied to the stopper 200 (e.g., to the medicament in the cartridge 114) or the force in the plunger rod 106. In some instances, a measurement signal is generated by a sensor positioned to experience the force of the plunger 106 on the stopper 200, where the measurement signal changes with the force of the stopper 200 relative to null movement of the plunger rod 106. This null movement could represent some resting pressure against the stopper 200 by the plunger rod 106 prior to initiation of a drug delivery operation. One skilled in the art will appreciate that a variety of pressure or force sensors will enable detection of the pressure or force on the stopper 200 or the force in the plunger rod 106 (e.g., a stress). In some cases, for example, the pressure or force sensor is a strain gauge or a diaphragm-type sensor using a change in capacitance to generate the measurement signal.

In some embodiments, different measuring methodologies are used to measure the position of the stopper 200. A certain signal is generated, which changes with the movement of the stopper 200 relative to a fixed position in the system or cartridge 114. This fixed position can be inside of the cartridge 114. In some cases, for example, the fixed position is on the septum area of the cartridge 114 or on another rigid wall of the cartridge 114. Alternatively, an element may be introduced into the cartridge for the purpose of providing a fixed reference. In other embodiments, the fixed reference could be outside of the cartridge outside, such as on the housing of the drug delivery device 100. In some embodiments, a sensor measures the change of a light signal by sending out the light from a light source (e.g., an LED) to the fixed area and receiving the remitted light with a photodetector. The intensity of the remission can be correlated to a distance. Another possibility is to measure the change of time needed for the signal (e.g., an acoustic signal) to travel from a sender to the fixed position back to a receiver positioned close to the sender. In another embodiment, the signal (optical, acoustic, capacitive etc.) can be sent out from a fixed position to a receiver in the moving stopper 200 to measure the change of the signal during stopper travel and correlate it to the stopper position in the cartridge 114.

In an example position sensing operation, the transmitter (e.g., one of the electronics devices 122, 124 or a component of the position sensor 342 of the electronics assembly 340) transmits an acoustic wave at a first time $t_1$. The first time $t_1$ (e.g., the transmission time of the acoustic wave) may be provided to an external device. The acoustic wave propagates from the transmitter in the stopper 200 toward the distal end of the cartridge 114 (i.e., the end having the cap 604) and is reflected off of (e.g., bounces off of) a surface of the cartridge 114 or a reflector disposed in the distal end of the cartridge 114. A reflection of the acoustic wave (e.g., a reflected wave) propagates from the distal end of the cartridge 114 toward a sensor in the stopper 200. The reflected wave is received at a second time $t_2$. The speed of the acoustic wave is a known speed of sound S in the medicament in the cartridge 114. The elapsed time between transmission and receiving of the acoustic wave is $t_2-t_1$. The elapsed time is multiplied by the speed of sound to determine the distance traveled by the wave from the transmitter, to the distal end of the cartridge 114, back to the sensor. The distance traveled is divided by two to determine the distance between the stopper 200 and the distal end of the cartridge 114, D. The volume V of medicament in the cartridge 114 (e.g., the volume of medicament enclosed in the cartridge 114 between the stopper 200 and the distal end) is determined by multiplying the determined distance by the cross-sectional area A of the cartridge 114 A. Thus, V=A*(t2−t1) *S/2. A detected difference in the determined volume of medicament in the cartridge 114 before and after a drug delivery operation corresponds to the dose administered to the patient.

Figure 3:
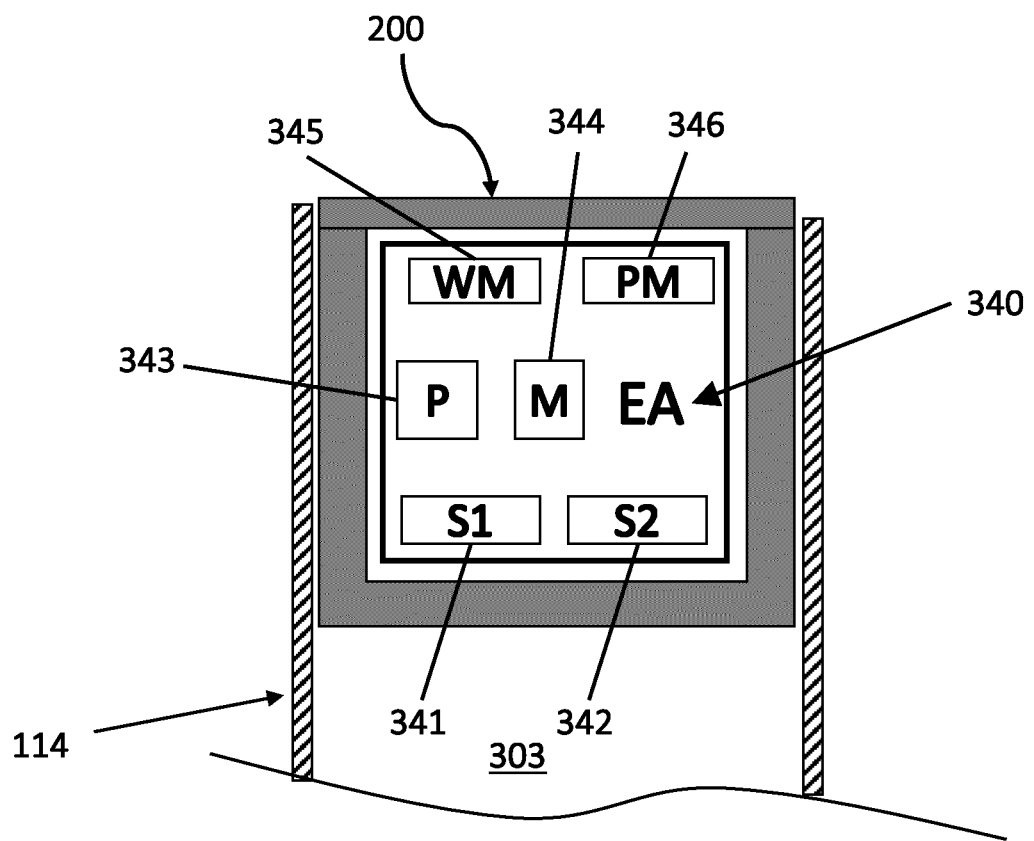
FIG. 3 is a cross-sectional schematic of internal components of an electronics assembly within the stopper of FIGS. 2A-2C.

FIG. 3 is a cross-sectional schematic of the internal components of an electronics assembly 340, which may be, for example, the electronic components 122, 124 shown in FIG. 1. The electronics assembly 340 is shown disposed in the stopper 200, which is itself installed in the open end of the cartridge 114. The electronics assembly 340 includes a pressure or force sensor 341, a position sensor 342, a processor 343, a memory 344, a wireless module 345, and power module 346. The pressure or force sensor 341 and position sensor 342 are arranged in the electronics assembly such that, when the electronics assembly 340 is disposed in the stopper 200, the position sensor 342 is able to send and receive a sensing signal into the inner volume 303 of the cartridge 114 or otherwise detect the position of the stopper 200 or the plunger rod 106, and the pressure or force sensor 341 is able to measure the force applied to the stopper 200 (or the electronics assembly) via the plunger 106 of the drug delivery device 100 or otherwise to detect the pressure in the plunger rod 106 or drive mechanism. The processor 343 is operably coupled to all of the elements of the electronics assembly 340 and controls activation of the pressure sensor 341, the position sensor 342, and the wireless module 345. The memory 344 stores instructions for use by the processor 343 in operating the components of the electronics assembly 340, as described above, and discussed in more detail with respect to the following figures.

While FIG. 3 illustrates the electronics assembly 340 in the stopper 200 with the pressure or force sensor 341 integral to the electronics assembly 340, in other instances the pressure or force sensor 341 is external to the electronics assembly (e.g., located at the point of contact by the plunger rod 106, attached to the plunger rod 106 itself, or in a drive mechanism of the drug delivery device 100 arranged to apply a force to the plunger rog 106). In additional, while FIG. 3 shows the electronics assembly 340 inside the stopper 200, one skilled in the art will appreciate that the electronics assembly 340, with or with an internal pressure or force sensor 341, can be located anywhere in the in drug delivery device 100 such that it can receive a signal from the pressure or force sensor 341.

In operation, the wireless module 346 is configured to communicate with an external electronic device in order to communicate information from the electronics assembly 340. The power module 346 is configured to provide electric power to the all of the components of the electronics assembly 340. In some embodiments, the electronics assembly 340 includes a capacitive device with includes capacitive circuitry configured to receive power wirelessly from, for example, a smartphone via a nearfield communication protocol (NFC) signal, or by a typical wireless charging device with other means of inductive loading, in order to provide energy to the module 346.

While FIG. 3 illustrates the electronics assembly 340 including a wireless module, in some instances there is no wireless connectivity, and the drug delivery device or the electronics assembly itself contains an alert mechanism configured to visually or audibly alert a user or provide certain information to a user. For example, a representative alert mechanism could be a display or series or LED lights arranged to illuminate a different color to a user based on the sensed pressure or force signal and a determined indication of the quality of a drug delivery operation. For instances, a blue light could indicate that the device is ready to use, an orange light could be illuminated while the drug delivery device is conducting the drug delivery operation, and then a green or red light could come on at the sensed completion of the drug delivery operation to indicate a successful or failed delivery operation, respectively. In other instances, the alert mechanism could produce different sounds or beeps to convey the same or different information as the visual alert mechanism.

FIG. 4A is a cross-sectional view of the electronics assembly 340 in the stopper 200, which is configured to be disposed in the drug delivery device 100. The stopper 200 includes the shell 202 holding the electronics assembly 340 and a cap 410 configured to seal the electronics assembly 340 into the stopper 200. FIG. 4A shows the cap 410 being installed 497 during assembly of the cartridge 114, prior to a medicament being filled in the inner volume 303 of the cartridge 114 or the cartridge 114 being installed in the drug delivery device 100. In this manner, FIG. 4A represents an assembly step where the electronics assembly 340 is, in some instances, configured to detect the assembly of stopper 200 or of the drug delivery device 100 using either the pressure or force sensor 341 or the position sensor 342 to detect movement of or a force applied to the stopper 200 indicative of the drug delivery device or cartridge 114 being ready for use.

In FIG. 4A, the electronics assembly 340 could be in a low power state until the pressure or force sensor 341 or position sensor 341 detects that the cartridge 114 is ready for use. In some embodiments, the pressure or force sensor 341 is configured to be an activation mechanism to trigger the electronics assembly 340 by either being installed in the stopper 200 or in the drug delivery device 100, as shown in FIG. 4B.

FIG. 4B is a cross-sectional view of the electronics assembly 340 and the stopper 200 disposed in the drug delivery device 100 in a ready-to-use configuration. FIG. 4B shows the cartridge 114 and the stopper 200 containing the electronics assembly 340, with the cartridge 114 installed in the drug delivery device 100, with the plunger 106 arranged to drive the stopper 200 and the electronics assembly 340 into the cartridge 114. The cap 410 has sealed the electronics assembly 340 within an interior region of the stopper 200. The inner volume 303 of the cartridge 114 has been filled with a medicament 40, and the electronics assembly 340 can, in some instances, sense (via sensing signals 471) the position of the stopper 200 in the inner volume 303.

In FIG. 4B the plunger 106 is driven by an actuator or drive mechanism of the drug delivery device 100 containing the cartridge 114. In operation, the plunger 106 is driven (as indicated by arrow 498) against the stopper 200 and applies a force to move the stopper 200 into the cartridge 114 in order to drive a portion of the medicament 40 from the cartridge 114. The pressure or force sensor 341 of the electronics assembly, in this example, is arranged to sense a pressure or force at location 471, where the cap 410 transmits the pressure or force from the plunger rod 106 to the electronics assembly 340. In other instances, the stopper 200 does not have a cap and the plunger rod 106 acts directly on the electronics assembly. In other instances, the pressure or force sensor 341 is remote from the electronics assembly and is for example, located between the stopper 200 and the plunger rod 106 or in any other suitable location to measure the force applied by the plunger rod 106 to the stopper 200 or to the medicament 40.

Figure 4C:
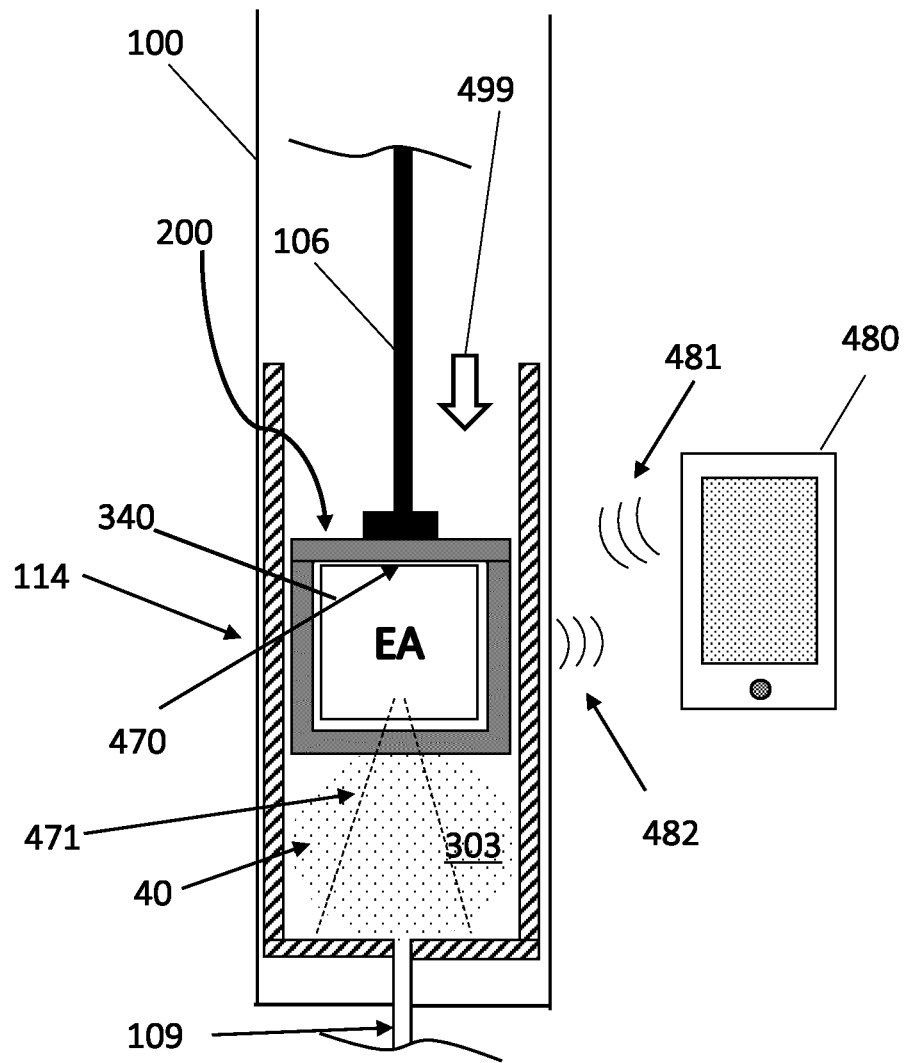
FIG. 4C is a cross-sectional view of the electronics assembly, stopper, and drug delivery device of FIG. 4B after a drug delivery operation.

FIG. 4C is a cross-sectional view of the electronics assembly 340, the stopper 200, and the drug delivery device 100 after a drug delivery operation. FIG. 4C shows the plunger 106 of the drug delivery device 100 contacting the stopper 200 and having driven the stopper 200 into the cartridge 114 (as shown by arrow 499) to conduct a drug delivery operation (e.g., an injection through the needle 109). In operation, the plunger rod 106 between FIG. 4B and FIG. 4C has applied a particular force profile on the stopper 200 at pressure or force sensing location 470 to position the stopper at the location shown in FIG. 4C, where this movement has also driven a portion of the medicament 40 from the cartridge 114. The pressure or force sensor 341 is arranged to generate a signal that represents the force at location 471 during the movement of the stopper 200 to the location shown. In this manner, the pressure or force sensor 341 provides to the electronics assembly 340 a time history of the pressure or force at that location 470 to enable the electronics assembly 340 to determine the quality of the drug delivery operation. In addition, in some embodiments, the sensing signal 470 is processed by the electronics assembly 340, and the electronics assembly 340 detects the movement of the stopper 200 or the fill level of the cartridge 114 after the illustrated drug delivery operation. The electronics assembly 340, using the sensed position of the stopper 200, can further improve the detection of the indication of the quality of the drug delivery operation by, for example, accurately measuring the dose the medicament 40 driven from the cartridge 114 based on the change in the sensed position of the stopper 200. Additionally, in some instances, and in response to the detection of the injection, the wireless module of the electronics assembly 340 is activated for a short duration to enable pairing with an external device 480.

FIG. 4C shows the external device 480 initiating a wireless communication 481 with the electronics assembly 340 and the wireless module of the electronics assembly 340 responding with a return wireless communication 482. In some instances, the return wireless communication 482 to the external device 480 includes the detected change in the position of the stopper 200 in the cartridge 114, the sensed pressure or force during the drug delivery operation, and the indication of the quality of the drug delivery operation. In some instances, the return wireless communication 482 includes a history of detected changes in the force or position, which enables the external device 480 to receive all or a portion of the prior drug delivery history of the cartridge 114 or the drug delivery device 100. The history of detected changes may include, for example, the previous change, multiple previous changes (e.g., a certain number or over a certain period of time), or a complete history of the detected changes. In some instances, the return wireless communication 482 includes position information, a sensed position history stored by the memory 344 of the electronics assembly 340, an indication of the quality of the drug delivery operation as determined by the electronics assembly 340, or a history of the indications of previous drug delivery operations.

In some instances, the return wireless communication 482 includes batch or expiration information of the medicament, cartridge, or drug delivery device. The return wireless communication 482 can also include any other parameters or changes sensed, detected, or determined by any or all components of the electronics assembly 340. In some embodiments, the return wireless communication 482 includes the state of the electronics assembly or of certain components of the electronics assembly, such as the remaining power. In some instances, the a plunger 106 is a plunger of a syringe where the cartridge 114 is the syringe housing (e.g., a single-use drug delivery device).

Figure 5:
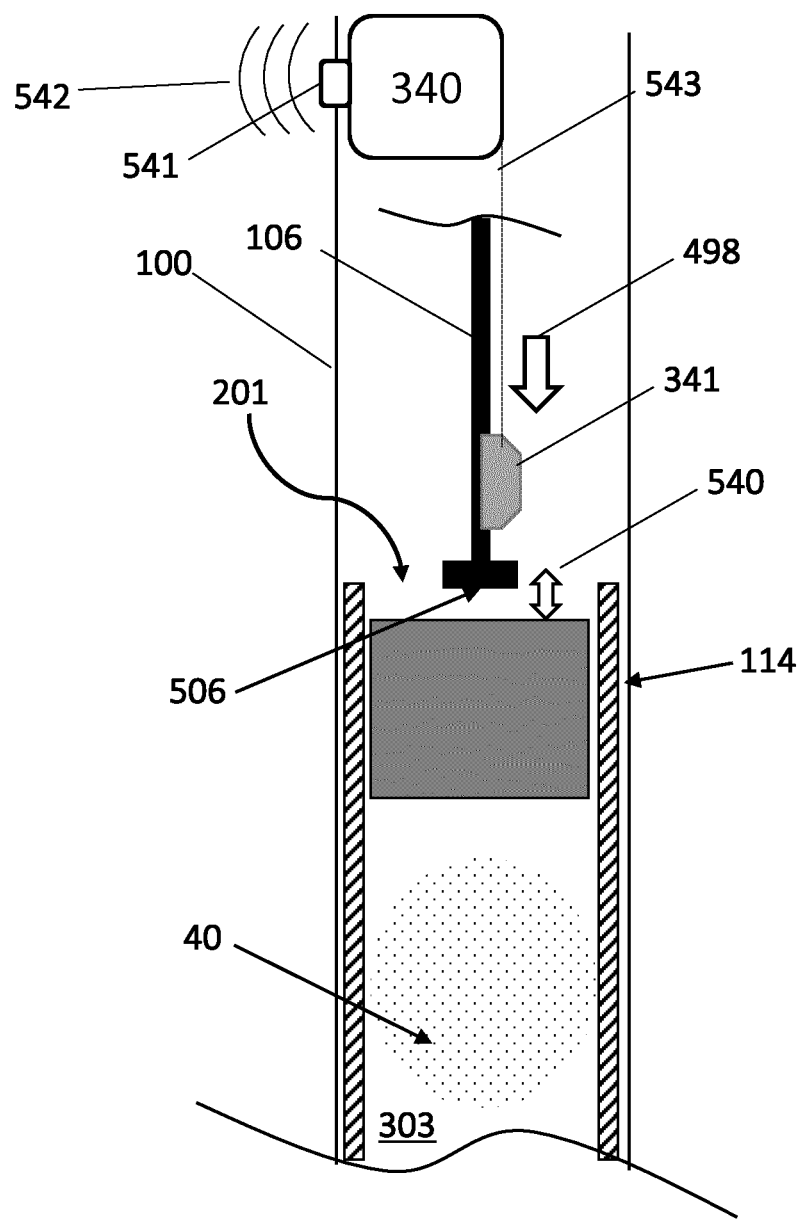
FIG. 5 is a cross-sectional view of a drug delivery device prior to a drug delivery operation, including an electronics assembly, a separate pressure sensor, a stopper, and an alert mechanism, where a pressure sensor is positioned external to the electronics assembly.

FIG. 5 is a cross-sectional view of the electronics assembly 340, stopper 201, and drug delivery device 100 having an alert mechanism 541, in a configuration prior to a drug delivery operation. FIG. 5 shows the electronics assembly 340 is located external to the stopper 201 and in the housing 101 of the drug delivery device 100. Additionally, the pressure or force sensor 341 is located on the plunger rod 106 in order to sense the stress or force applied by the plunger rod 106 to the stopper 201 with an electrical connection 543 to the electronics assembly 340. The stopper 201 here is a generic cartridge stopper without an internal electronics assembly, as shown above. FIG. 5 also illustrates the priming gap condition mentioned above, where the head 506 of the plunger rod 106 is spaced a distance 540 away from the stopper 201, such that an initial movement of the plunger rod 106 will displace the plunger rod 106 without applying a force to the stopper 201. In some instances, the electronics assembly 340 also receives a signal from a sensor configured to detect a position of a dose setting mechanism (e.g., dosage knob 112), to enable the electronics assembly to be aware of the expected dose that the drug delivery device 100 is attempting to delivery in the drug delivery operation. In drug delivery devices 100 where different doses are able to be delivered, this sensing of the a position of a dose setting mechanism (or just a general receiving of a signal corresponding to a set dose), enables the electronics assembly to determine if the sensed pressure or force corresponds to an expected sensed pressure or force that corresponds to the set dose.

In FIG. 5 the plunger 106 is driven by an actuator or drive mechanism of the drug delivery device 100 containing the cartridge 114 for a predetermined distance based on a dose of the medicament 40 to be expelled from the cartridge 114. In operation, the plunger 106 is driven (as indicated by arrow 498) against the stopper 200 and applies a force at location 506 to move the stopper 201 into the cartridge 114 in order to drive a portion of the medicament 40 from the cartridge 114. The pressure or force sensor 341 is arranged to sense the stress in the plunger rod 106 during the drug delivery operation and provide the measured stress to the electronics assembly 340, then determines a quality of the drug delivery operation and operates the alert mechanism 541 to provide an alert signal 542, as discussed above, to a user of the drug delivery device 100.

Figure 6:
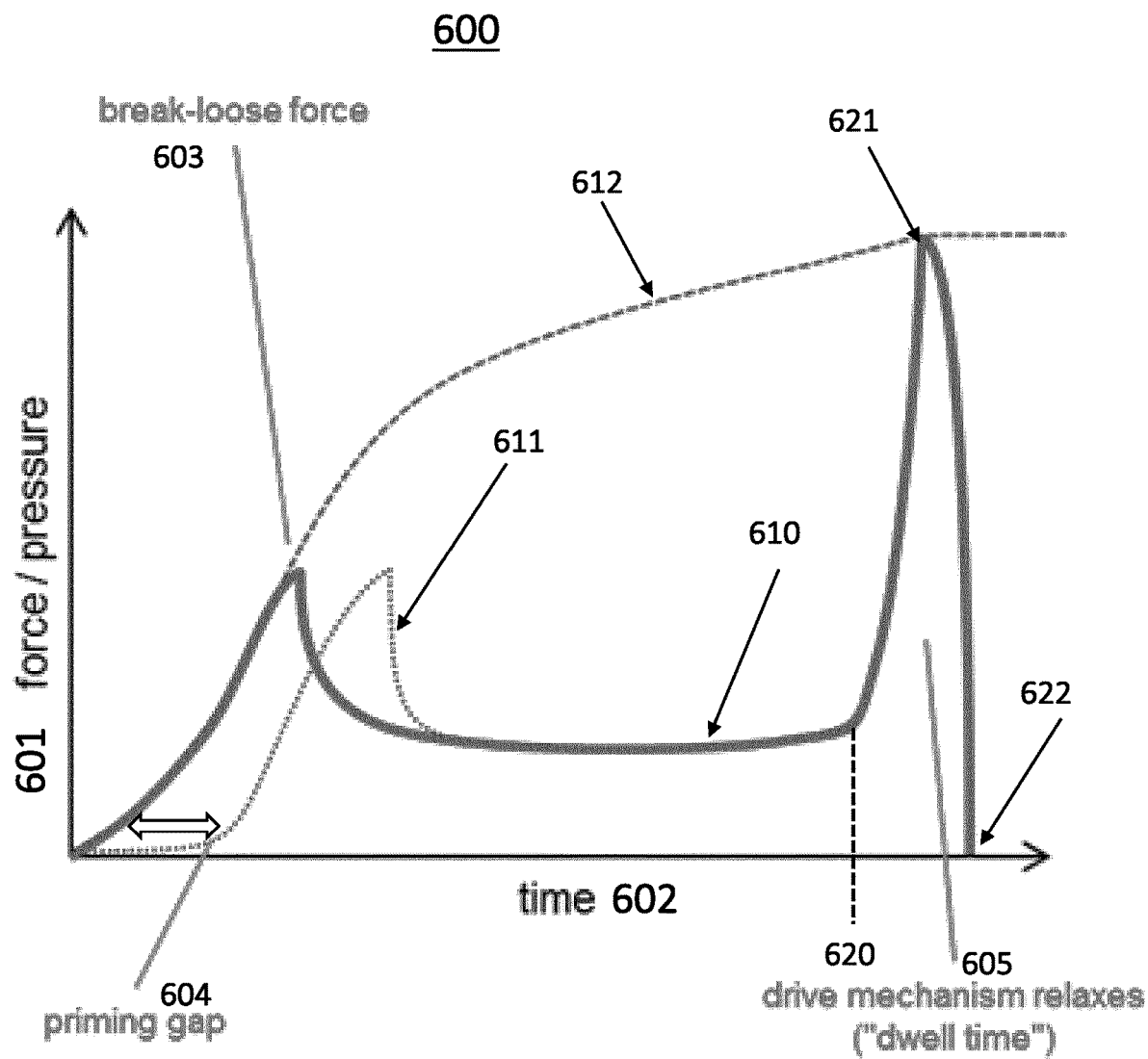
FIG. 6 is a force vs. time graph of sensed pressure during a drug delivery operation of the drug delivery device.

FIG. 6 is a force vs. time graph of sensed pressure or force during a drug delivery operation of the drug delivery device 100 as discussed above. FIG. 6 shows sensed pressure or force 601 vs. time 602 during three different drug delivery operations. In a first drug delivery operation (bold line), a sensed force 610 peaks initially at a break-loose force 603, which represents the start of the movement of the stopper 200 in the cartridge 114. Continuing in time, the sensed force 610 decreases as the stopper 200 moves in the cartridge 114 under the force of the plunger rod 106, until, in this example, the stopper 200 reaches the terminal end of the cartridge 114 at time 620, at which point the full force 621 of the plunger rod 106 is shown in the sensed force 610. Finally, the drive mechanism and drug delivery device 100 relaxes 605 until the sensed pressure or force 610 renormalizes (e.g., returns to the initial value) at time 622, which indicates the completion of the drug delivery operation. In a second drug delivery operation (thin dotted line), a sensed force 611 rises later than the sensed force 610 of the first drug delivery operation, as a result of, for example, a delay in the plunger rod 106 contacting the stopper 200. The delay of the rise of the sensed pressure or force 611 an the delay of the sensed pressure or force 611 reaching the break loose force 603 is clearly identified able with respect to the nominal first sensed pressure or force 611. In a third drug delivery operation (thick dotted line), a sensed force 612 rises beyond the break loose force 603 during the drug delivery operation until the sensed pressure or force 612 peaks at the full force 621 of the plunger rod 106. In this third drug delivery operation, the continued rise of the sensed force 612 indicates that a large force was applied to the plunger 200 during the drug delivery operation, which indicates that either the stopper 200 did not move in the cartridge 114, or that there was extra resistance to the movement of the stopper 200, which can result from, for example, a blocked or clogged needle 109 or drug delivery pathway from the cartridge 114.

In operation, the electronics assembly 340 receives the sensed pressures or forces 610, 611, 612 and determines an indication of the quality of each drug delivery operation resulting in the sensed pressures or forces 610, 611, 612. For example, the memory 344 may store a normal pressure curve (as, for example, a function or a plurality of pressure values at different times) of a normal drug delivery operation, and the processor 343 compares the sensed pressures 610, 611, 612 to the normal pressure curve at different times of the drug delivery operation to detect the priming gap in the second drug delivery operation, and the blockage in the third drug delivery operation. The electronics assembly 340 generates an indication of the quality of the drug delivery operations corresponding to the sensed pressures 610, 611, 612, where the indication represent a normal, priming gap, and blocked quality, respectively.

Figure 7A:
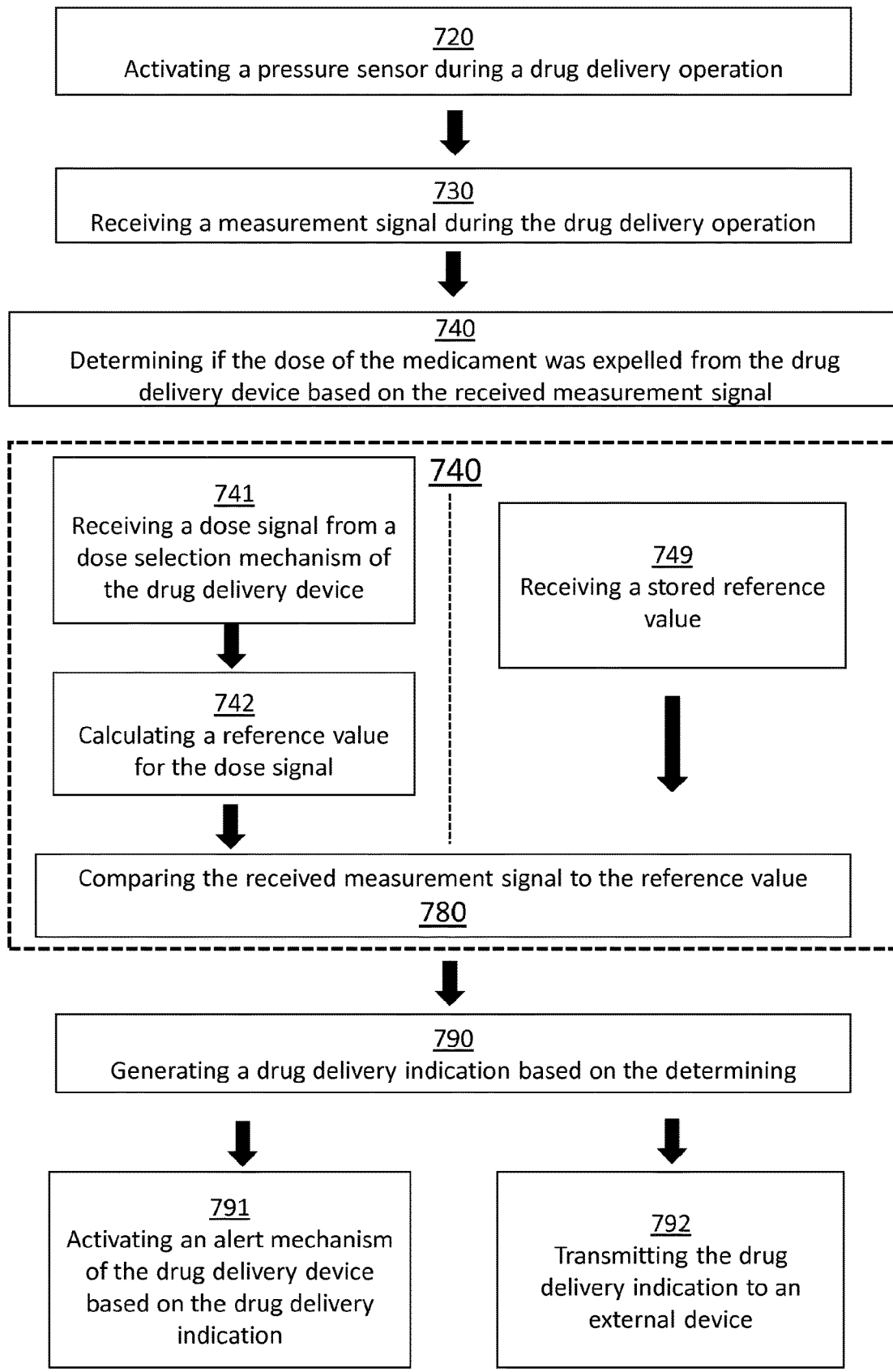
FIG. 7A is a flowchart depicting a method of determining a status of a drug delivery operation based on a sensed pressure.

FIG. 7A is a flowchart depicting a method 700 determining the status of a drug delivery operation based on a sensed pressure. In some examples, the method 700 includes a series of instructions coded into the memory 344 of the electronics assembly 340. At a first step 720, the pressure sensor 341 is activated during a drug delivery operation and a measurement signal is generated that corresponds to, for example, a sensed pressure on the stopper 200 or the drive mechanism 106 while a set dose of medicament is dispensed from the drug delivery 100, as described above. In the next step 730, the pressure sensor 341 provides the measurement signal to the processor 343, where the processor 343, in a following step 740, determines if the dose of the medicament 40 was expelled from the drug delivery device 100 based on the received measurement signal. The determination at step 740 can be based on different comparison to expected values. For example, in a first aspect, the comparing at step 740 includes a first step 741 of receiving a dose signal from the dose selection mechanism 112 that contains an indication of the actual dose set by the user of the drug delivery device 100. In a subsequent step 742, a reference value (e.g., an expected pressure signal) is calculated based on the received indication of the dose. Alternatively, in a second aspect, the comparing at step includes a single step 749 of receiving a stored reference value for the pressure signal. For example, if the drug delivery device 100 is a single-dose device, then there may be a singular range of expected pressure signals for a successful dose dispensing operation.

Figure 7B:
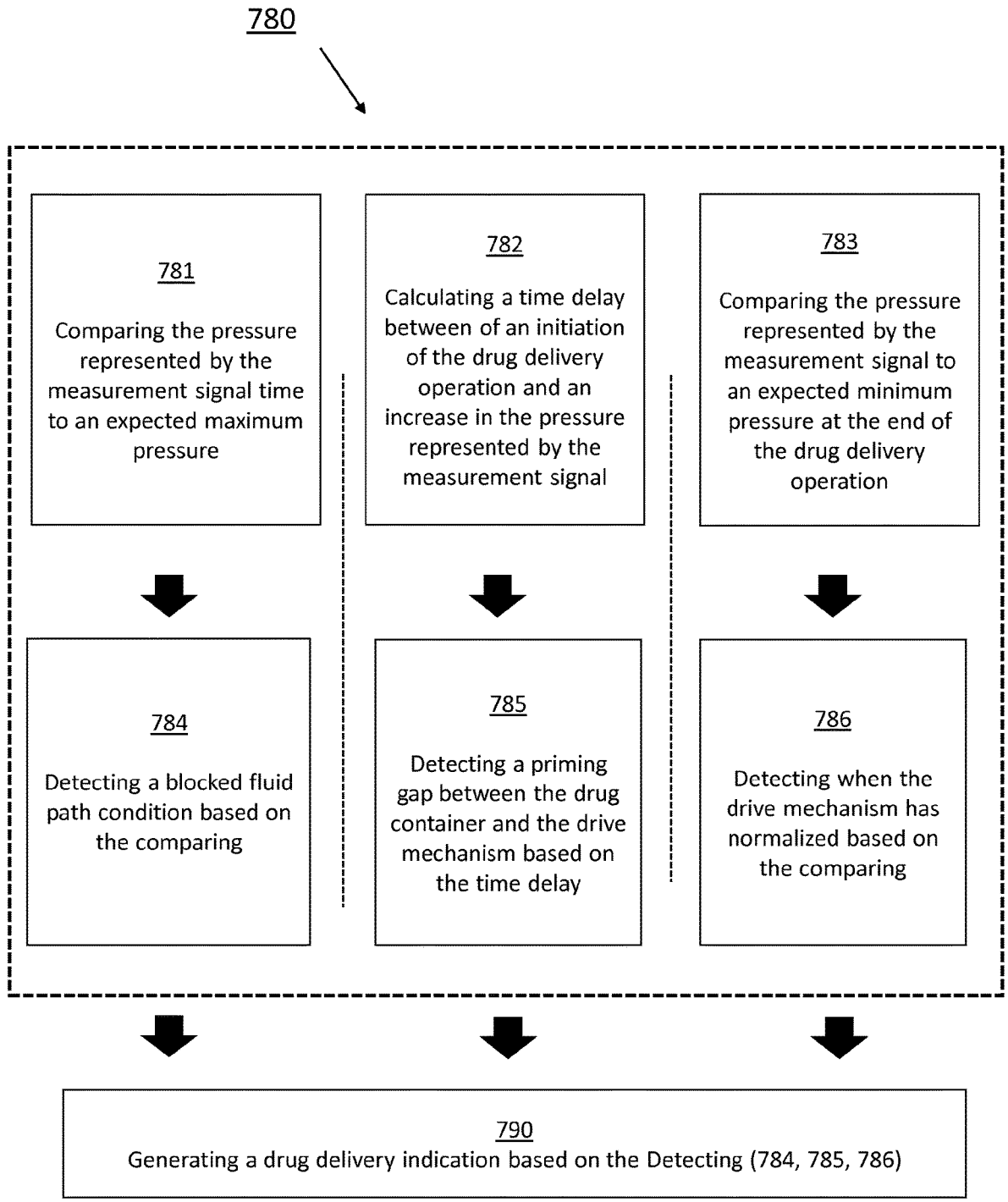
FIG. 7B is a flow chart of the steps conducted for determining various drug delivery indications in step 780 of FIG. 7A.

In other examples, there may be an expected range of pressure signals based on various possible doses. In either aspect, a position senor 342 may be used to assist in the calculation or look-up of the value or values of the reference signal. In either aspect, a final step 780 of comparing the received measurement signal to the reference value is done to identify if one or more possible failures are indicated by the comparison, as shown in FIG. 7B. Continuing to refer to FIG. 7A, at step 790, the results of the comparing step 780 are used to generate a drug delivery indication. For example, a successful injection or drug delivery may be indicated if the comparisons are within specific tolerances, else, for example, an incomplete or failed injected may be indicated, as well as a possible reason for the failure (e.g., a blockage or a priming gap). In some instances, the drug delivery indication may include an estimation or calculation of the dose of medicament expelled during the drug delivery operation. Finally, the drug delivery indication is used at step 791 to activate an alert mechanism 541 or at step 792 to transmit the drug delivery indication to an external device 480 in order to present the information of the drug delivery indication to the user and/or to store the drug delivery indication.

FIG. 7B is a flow chart of the steps conducted for determining various drug delivery indications in step 780. For example, at step 781 a comparison of the expected pressure from steps 742 or 749 is compared to a maximum pressure signal generated by the pressure sensor 341 and, if the received maximum pressure occurs too early or remains too long after the expected end of the drug delivery operation (see, for example trace 612 for FIG. 6), then at step 784 a blocked fluid path condition is detected at step 784. Another failure mode, a priming gap, is detected by first calculating, at step 782, a time delay between an initiation of the drug delivery operation and an increase in the received pressure signal. The existence of priming gap is detected at step 785 based on the existence of length of the time delay (see, for example, the delay 604 of FIG. 6) between the initiation of the drug delivery operation and the increase in the pressure signal. In addition, the detection step 780 may include the ability to determine when the drive mechanism 106 has relaxed at the end of an injection, such that all of the medicament of the desired dose has been expelled from the drug delivery device 100. To determine when the drug delivery device 100 relaxes post drug delivery, a step 783 of comparing the received pressure signal to an expected minimum pressure at the end of the drug delivery operation is conducted. Subsequently, at step 786, a determination is made regarding when and if the minimum pressure of the received signal indicates that the drug delivery operation is completed. In some aspects, this determination at step 786 is done in real time in order to generate an alert to the user that indicates completion of the drug delivery operation.

Figure 8:
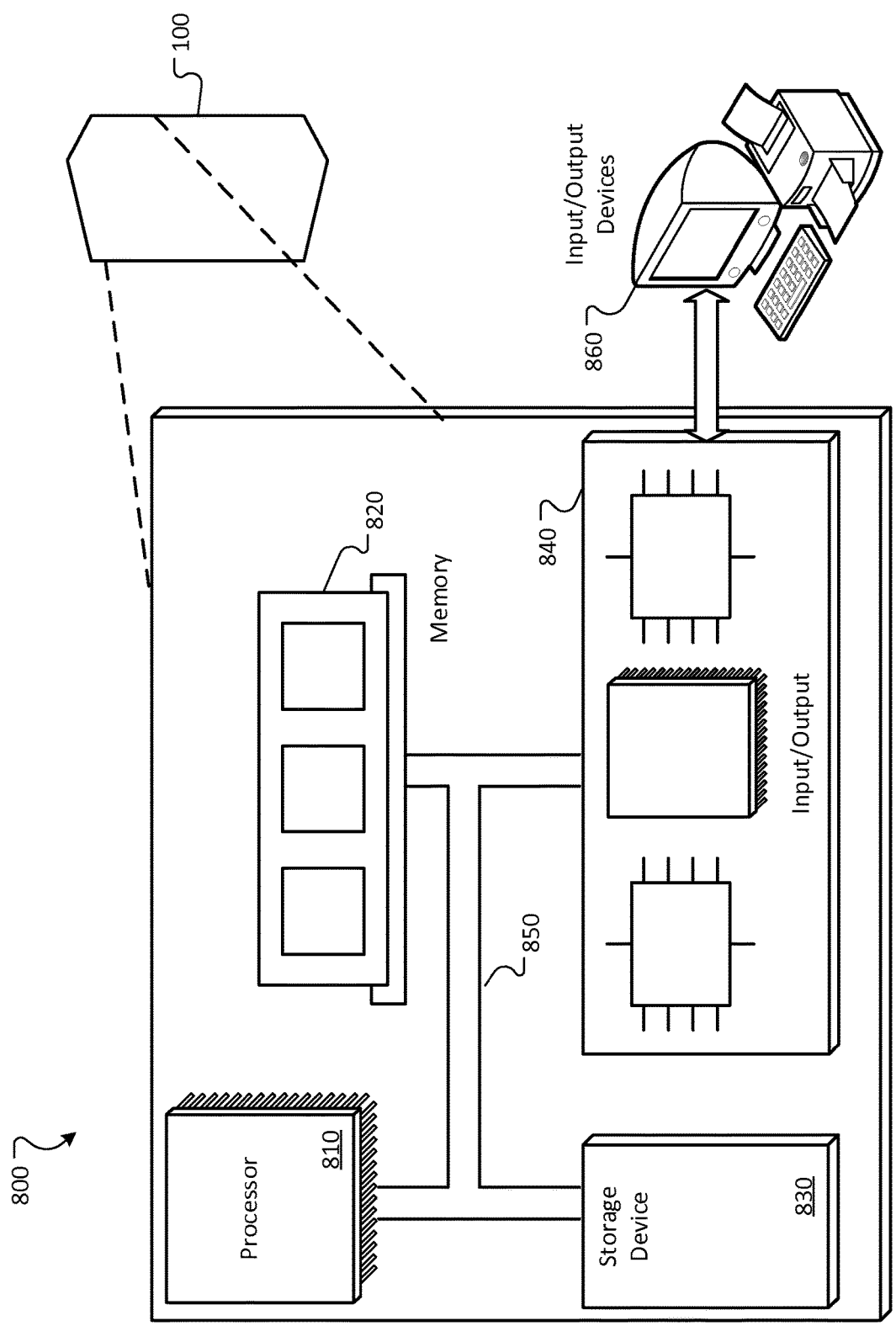
FIG. 8 is an illustration of a processor for use in aspects of the present disclosure.

FIG. 8 is a block diagram of an example computer system 800. For example, referring to FIG. 3 could be an example of the electronics assembly 340 described here, as could a computer system used by any of the users to communicate the electronics assembly 340. The system 800 includes a processor 810, a memory 820, a storage device 830, and one or more input/output interface devices 840. Each of the components 810, 820, 830, and 840 can be interconnected, for example, using a system bus 850.

The processor 810 is capable of processing instructions for execution within the system 800. The term "execution" as used here refers to a technique in which program code causes a processor to carry out one or more processor instructions. In some implementations, the processor 810 is a single-threaded processor. In some implementations, the processor 810 is a multi-threaded processor. In some implementations, the processor 810 is a quantum computer. The processor 810 is capable of processing instructions stored in the memory 820 or on the storage device 830. The processor 810 may execute operations such as processing of the pressure sensor signal and the determining the quality of the drug delivery operation.

The memory 820 stores information within the system 800. In some implementations, the memory 820 is a computer-readable medium. In some implementations, the memory 820 is a volatile memory unit. In some implementations, the memory 820 is a non-volatile memory unit.

The storage device 830 is capable of providing mass storage for the system 800. In some implementations, the storage device 830 is a non-transitory computer-readable medium. In various different implementations, the storage device 830 can include, for example, a hard disk device, an optical disk device, a solid-state drive, a flash drive, magnetic tape, or some other large capacity storage device. In some implementations, the storage device 830 may be a cloud storage device, e.g., a logical storage device including one or more physical storage devices distributed on a network and accessed using a network, via communication with the external electronic device 480. In some examples, the storage device may store long-term data, such as reference pressure or force values, drug delivery device identification, medicament identification or expiration, or history of one or more sensors in the drug delivery device 100 (e.g., a position sensor or the pressure or force sensor 341). The input/output interface devices 840 provide input/output operations for the system 800. In some implementations, the input/output interface devices 840 can include one or more of a network interface devices, e.g., an Ethernet interface, a serial communication device, e.g., an RS-232 interface, and/or a wireless interface device, e.g., an 802.11 interface, a 3G wireless modem, a 4G wireless modem, etc. A network interface device allows the system 800 to communicate, for example, transmit and receive data such as drug delivery device identification, medicament identification or expiration, a pressure or force signal, or an indication of the quality of the drug delivery operation, as shown in FIG. 4C, e.g., using the return wireless communication 482. In some implementations, the input/output device can include driver devices configured to receive input data and send output data to other input/output devices, e.g., keyboard, printer and display devices 860. In some implementations, mobile computing devices, mobile communication devices, and other devices can be used.

Referring to FIG. 7, the pressure or force sensing and detection methods can be realized by instructions that upon execution cause one or more processing devices to carry out the processes and functions described above, for example, processing of pressure or force sensor data. Such instructions can include, for example, interpreted instructions such as script instructions, or executable code, or other instructions stored in a computer readable medium.

Aspects of the electronics assembly 340 as shown in FIG. 3 can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the system 800 is contained within a single integrated circuit package. A system 800 of this kind, in which both a processor 810 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 840.

Although an example processing system has been described in FIGS. 6 and 7, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry.

Described above are devices are operations that require the use of energy provided to electronic circuitry in cartridge systems (for example, those disclosed herein) using a power module (PM), which may include, for example, batteries or other power storage devices, using such technologies as lithium ion, nickel-metal hydride, nickel-cadmium, zinc-air, or the like.

Aspects of the systems disclose above enable medical injectors to employ 'smart' technologies by way of an attached of the included electronic components (e.g. RFID, sensor) to give a certain features to a cartridge of a drug delivery device (e.g. of a pen-type injector). When integrating electronics into the stopper of a cartridge, a one or more components may be active (e.g., a sensor to measure certain properties of the injector or cartridge) and require an energy source, which typically could be a battery. One alternative is to use a means of energy harvesting as a power source replacement for a battery.

Embodiments of the present disclosure can also apply to prefilled single and double chamber syringes that may not use a cartridge. The examples described above for electronics assemblies in the stopper of a cartridge can also be used with other drug containers, such as disposable prefilled syringes or reusable/refillable cartridges. In some instances, the electronics assembly is contained in the cartridge or in the drug delivery device in a manner enabling the electronics assembly to sense a change in the fill level of the cartridge or syringe after an injection. In some instances, components of the electronics assembly are located outside of the stopper or in different parts of the cartridge or drug delivery device.

Some of the features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the present disclosure have been described. Nevertheless, it will be understood that various modifications may be made without departing from the spirit and scope of the present disclosure. Accordingly, other embodiments are within the scope of the following claims.

What is claimed is:

1. A drug delivery device comprising:
   a housing;
   a drug container arranged to be contained in the housing of the drug delivery device, the drug container comprising a stopper configured to contain a medicament in the drug container;
   a drive mechanism configured to exert a force onto the stopper of the drug container to drive the stopper into the drug container and expel a dose of the medicament from the drug delivery device during a drug delivery operation;
   a processor;
   a sensor configured to measure the force applied by the drive mechanism and output a measurement signal to the processor;
   at least one non-transitory computer readable medium storing instructions operable to cause the processor to perform operations comprising:
      activating the sensor during the drug delivery operation,
      receiving the measurement signal during the drug delivery operation,
      determining whether at least a portion of the medicament was expelled from the drug delivery device based on the received measurement signal, and
      generating a drug delivery indication in response to determining that at least a portion of the medicament was expelled, wherein the drug delivery indication is generated based on the measurement signal and indicates a calculated amount of medicament that was expelled and/or identifies one or more failures in the drug delivery operation, wherein the drug delivery indication is one of a plurality of possible drug delivery indications; and
      activating an alert mechanism configured to provide a particular alert associated with the drug delivery indication, the particular alert being an audible, tactile, or visible alert to a user of the drug delivery device,
      wherein the alert mechanism is configured to provide different alerts, wherein each of the different alerts corresponds to a respective drug delivery indication of the plurality of possible drug delivery indications.

2. The drug delivery device of claim 1, wherein the non-transitory computer readable medium stores a reference measurement signal for the dose, and wherein the determining if the dose of the medicament was expelled includes comparing the received measurement signal to the reference measurement signal.

3. The drug delivery device of claim 1, wherein the drug delivery device comprises a dose selection mechanism configured to set the dose and output a dose signal to the processor corresponding to the dose,
   wherein the operations further comprise receiving the dose signal and calculating a reference measuring signal for the dose, and
   wherein the determining if the dose of the medicament was expelled includes comparing the received measurement signal to the reference measurement signal.

4. The drug delivery device of claim 1, wherein the operations further comprise comparing a force or pressure represented by the measurement signal to an expected maximum force or pressure, and
   wherein the determining if the dose of the medicament was expelled from the drug delivery device includes detecting a blocked fluid path condition based on the comparing.

5. The drug delivery device of claim 1, wherein the operations further comprise:
   calculating a time delay between an initiation of the drug delivery operation and an increase in a pressure or force represented by the measurement signal,
   wherein determining if the dose of the medicament was expelled from the drug delivery device includes detecting a priming gap between the drug container and the drive mechanism based on the time delay.

6. The drug delivery device of claim 1, wherein the operations further comprise comparing a pressure or force represented by the measurement signal to an expected minimum pressure or force at an end of the drug delivery operation,
   wherein the determining if the dose of the medicament was expelled from the drug delivery device includes determining when an internal force in the drive mechanism has normalized based on the comparing.

7. The drug delivery device of claim 1, comprising a wireless module configured to transmit a wireless signal to an external device, and wherein the operations further comprise:
   transmitting the drug delivery indication to the external device.

8. The drug delivery device of claim 1, wherein the alert mechanism is configured to alert the user of a successful drug delivery operation and/or of any issues detected during the drug delivery operation based on the measurement signal.

9. The drug delivery device of claim 1, comprising:
   a position sensor configured to detect a position of one or more of the stopper and the drive mechanism and output a position signal to the processor,
   wherein the operations further comprise receiving the position signal at least one of: before, during, and after the drug delivery operation, and
   wherein determining if the dose of the medicament was expelled from the drug delivery device is based on the received measurement signal and the received position signal.

* * * * *